United States Patent [19]

Rounbehler et al.

[11] 4,301,114
[45] Nov. 17, 1981

[54] MOLECULAR SIEVE TRAP FOR NITROGEN COMPOUND DETECTION

[75] Inventors: David P. Rounbehler, Concord; John W. Reisch, Brookline, both of Mass.

[73] Assignee: Thermo Electron Corporation, Waltham, Mass.

[21] Appl. No.: 164,476

[22] Filed: Jun. 30, 1980

[51] Int. Cl.³ .................. G01N 21/64; G01N 31/12
[52] U.S. Cl. .................. 422/52; 23/230 PC; 55/75; 55/68; 422/78; 422/89
[58] Field of Search ............ 23/230 PC; 422/52, 78, 422/80, 89; 55/68, 75

[56] References Cited

U.S. PATENT DOCUMENTS

| | | | |
|---|---|---|---|
| 3,763,877 | 10/1973 | Lieb | 137/117 |
| 3,856,473 | 12/1974 | Dillon | 250/207 |
| 3,941,573 | 3/1976 | Chapel | 55/316 |
| 3,973,610 | 8/1976 | Fine | 23/230 PC |
| 3,996,002 | 12/1976 | Fine | 23/230 PC |
| 4,153,429 | 5/1979 | Matthews | 55/75 X |
| 4,190,424 | 2/1980 | Armond et al. | 55/75 X |

OTHER PUBLICATIONS

*Union Carbide Brochure on Molecular Sieves*, pp. 3–6, 16–18, (1978).

Primary Examiner—Ronald Serwin
Attorney, Agent, or Firm—Herbert E. Messenger; James L. Neal

[57] ABSTRACT

A molecular sieve trap is disclosed for selective trapping of substances in a gas stream, the trap being particularly useful in systems for detecting nitrogen compounds such as N-nitrosamines or nitrogen oxides in a sample. The trap comprises a cartridge containing a packing of a granular adsorbent molecular sieve material with a carefully controlled pore size of about ten angstroms and a preference for adsorbing polar substances. The packing readily passes NO and $NO_2$ gases in a gas stream directed through the trap while trapping and retaining larger and/or more polar molecules such as those of double-bonded carbon compounds and sulfur compounds which could otherwise interfere with subsequent measurement of the NO or $NO_x$ content of the gas stream. An N-nitroso compound detection system incorporating the molecular sieve trap is described wherein the molecular sieve trap is interposed between a pyrolyzer and a chemiluminescent NO detector to selectively trap substances in the reactor effluent. Also disclosed is a $NO_x$ detection system having a molecular sieve trap in a sample inlet line of a $NO_x$ detector.

21 Claims, 12 Drawing Figures

Fig. 9. SYSTEM WITH MOLECULAR SIEVE TRAP

Fig. 8. PRIOR ART SYSTEM WITH COLD TRAP

Fig. 7. PRIOR ART SYSTEM WITHOUT TRAP

MOLECULAR SIEVE TRAP FOR NITROGEN COMPOUND DETECTION

CROSS-REFERENCE TO RELATED PATENT

The subject matter of the present invention is related to that disclosed in U.S. Pat. No. 3,996,002, "Method and Apparatus for Measuring the N-nitroso Compound Content of a Sample", issued Dec. 7, 1976, to David H. Fine, assigned to the assignee of the present invention. The material disclosed in that patent is incorporated herein by reference thereto.

BACKGROUND OF THE INVENTION

The invention relates to apparatus for selectively trapping substances in a gas stream, and to systems incorporating selective traps, particularly systems for detecting nitrogen-containing compounds such as nitroso compounds, amines, nitrofurans, nitrotoluenes, and nitrogen oxides present in liquid or gaseous samples.

Among the nitrogen-containing compounds whose detection has become of increasing interest are N-nitroso compounds or N-nitrosamines, which have the general formula wherein $R_1$ and $R_2$ are the same or different organic radicals including those radicals which together with the non-nitroso N of the depicted N—NO bond constitute a nitrogen heterocyclic radical. Many of these compounds are highly carcinogenic with respect to animals. Although their effect on humans is current unknown, efforts to monitor the presence of N-nitroso compounds have increased, particularly since these compounds have been found in trace quantities in many materials which are contacted or taken internally by humans, including artificial food additives, tobacco smoke, beer, pesticides, and the atmosphere.

Considerable work has been conducted on detection and measurement of N-nitroso compounds. One system which has been successfully used to measure the N-nitrosamine content of a sample is described and claimed in the above-referenced U.S. Pat. No. 3,996,002. The system described therein includes (a) a liquid or gas chromotograph for separating in time the N-nitroso compound portion of a sample from portions containing compounds such as nitrates or nitrites; (b) a non-catalytic pyrolyzer for selectively breaking the N—NO bond in the N-nitroso compounds to selectively liberate nitric oxide (NO) gas; and (c) a NO detector for measuring the amount of NO gas liberated.

In some embodiments of the above-noted system, a cold trap is included between the pyrolyzer and NO detector for eliminating from the effluent of the pyrolyzer certain trace contaminants, carrier gases, and the pyrolysis products associated with certain solvents. A typical cold trap used in N-nitrosamine detection comprises a conduit immersed in a bath of a cryogenic medium and having an inlet and outlet for throughflow of pyrolyzer effluent. The cryogenic medium-e.g., mixtures such as dry ice and acetone, or liquid nitrogen and pentane, or liquid nitrogen and isooctane-is selected to maintain a temperature sufficiently low to condense gases in the pyrolyzer effluent whose presence in the NO detector could interfere with accurate detection of NO. This temperature must, however, be sufficiently above the freezing point of NO (about -162° C.) to permit all of the NO gas to pass through the cold trap and into the NO detector. The condensation of potentially interfering gases and retention of their condensate in the cold trap prevents their erroneous contribution to the N-nitroso compound content signal of the detector. This trapping thus helps to provide accurate detection of N-nitroso compounds and also permits the use of solvent programming and/or the use a greater variety of carrier gases in the system.

While the foregoing patented system has proven very effective in measuring the concentration of N-nitrosamines and other nitrogen-containing compounds in liquid or gaseous samples, the cold traps used as part of the system present certain drawbacks. For example, the traps use cryogenic agents which are relatively expensive and require careful handling. The cold traps also require considerable upkeep such as the periodic removal of condensate and the addition of cryogenic agent to maintain desired cold trap temperatures. The cold traps inherently do not remove gases with freezing points lower than the temperature maintained in the traps. Also, they may not remove all of the gases with higher freezing points because during flow of the gas through the trap there may be insufficient contact between some of the gas and the chilled environment of the trap. In addition, if particulate matter such as dust or dirt is present in the pyrolyzer effluent, it may pass through a cold trap, decreasing detection sensitivity and necessitating frequent cleaning of optical components of the NO detector. Moreover, the cold traps do not readily provide an indication when their performance as trapping devices deteriorates.

Accordingly, it is an object of the invention to provide an improved trap for selectively removing substances from a gas stream.

It is also an object of the invention to provide a system for measuring the content of certain nitrogen-containing compounds of a sample.

It is an object of the invention to provide a trap which, in an apparatus which determines nitrogen compound content by selective liberation in a reactor of NO gas from a sample followed by measurement of the NO gas liberated, an improved trap for removing from the reactor effluent certain substances which could interfere with accurate measurement of the NO gas liberated.

It is a particular object of the invention to provide an improved system for detecting N-nitroso compounds and having a trap according to the preceding objects which is also inexpensive, convenient to use, and requires little or no maintenance.

It is also an object of the invention to provide an improved system for detecting oxides of nitrogen in a gas stream.

SUMMARY OF THE INVENTION

The invention concerns a molecular sieve trap for the selective trapping of substances in a gas stream, and systems for detecting nitrogen compounds which include the molecular sieve trap as an essential component.

The trap of the invention comprises a cartridge which contains a packing of a granular adsorbent material such as a zeolite or molecular sieve material having a precisely controlled pore size and a selected particle size. A preferred packing material comprises 60 to 80 mesh size particles of Type 13X Union Carbide molecular sieve material, a synthetic, crystalline, activated alumino-silicate having a precisely controlled pore size of about ten angstroms. When a gas stream containing NO and/or $NO_2$ gas is directed through the trap, the trap operates as a selective filter to readily pass these gases through the packing while trapping and retaining certain substances in the gas stream which could otherwise interfere with subsequent measurement of NO or $NO_2$ gas.

In accordance with one preferred embodiment of the invention, a $NO_x$ detection system is provided incorporating a molecular sieve trap in a sample inlet line of a chemiluminescent analyzer. The trap acts as a filter to readily pass NO and $NO_2$ gases in a gaseous sample for subsequent detection while trapping substances which could interfere with accurate operation of the analyzer by mimicking the presence of NO and $NO_2$ and thus indicating erroneously high levels of these gases.

In accordance with another embodiment of the invention, a nitrogen compound detection system is provided which incorporates a molecular sieve trap upstream of a NO detector. A preferred detection system includes a chromotograph for receiving a liquid or gaseous sample and separating it into an effluent portion containing nitrogen compounds to be detected and an effluent portion without such compounds; a reactor such as a pyrolyzer for selectively liberating NO gas from the nitrogen compounds to be detected; an NO detector for measuring the amount of NO gas liberated; and a molecular sieve trap located between the reactor and the NO detector for passing NO gas in the reactor effluent while trapping substances including double-bonded carbon compounds, sulfur compounds such as hydrogen sulfide, vinyl halides, and dust and dirt particles. The removal of such substances from the reactor effluent prevents them from erroneously contributing to the output signal of the NO detector. For example, during operation of a preferred system for detecting N-nitroso compounds which comprises, in seris, a gas chromatograph, a pyrolyzer, a molecular sieve trap and a chemiluminescent NO detector, the trapped compounds are unavailable to participate in chemiluminescent reactions which could mimic the behavior of NO gas. False NO detector output signals are thereby avoided. Also, background noise level is reduced, increasing the sensitivity of the system and thus permitting its use in the detection of very low levels of N-nitroso compounds.

In addition to facilitating accurate measurement of nitrogen compounds such as N-nitroso compounds in a sample, the molecular sieve trap of the invention is considerably less expensive than cold traps used in prior art detection systems and is easy to install and replace. Trap maintenance is minimal and is simplified in that during operation of a system including the trap, the output signal of the NO detector provides a clear indication when effectiveness of the molecular sieve trap diminishes.

DETAILED DESCRIPTION OF PREFERRED EMBODIMENTS OF THE INVENTION

Figure 1:
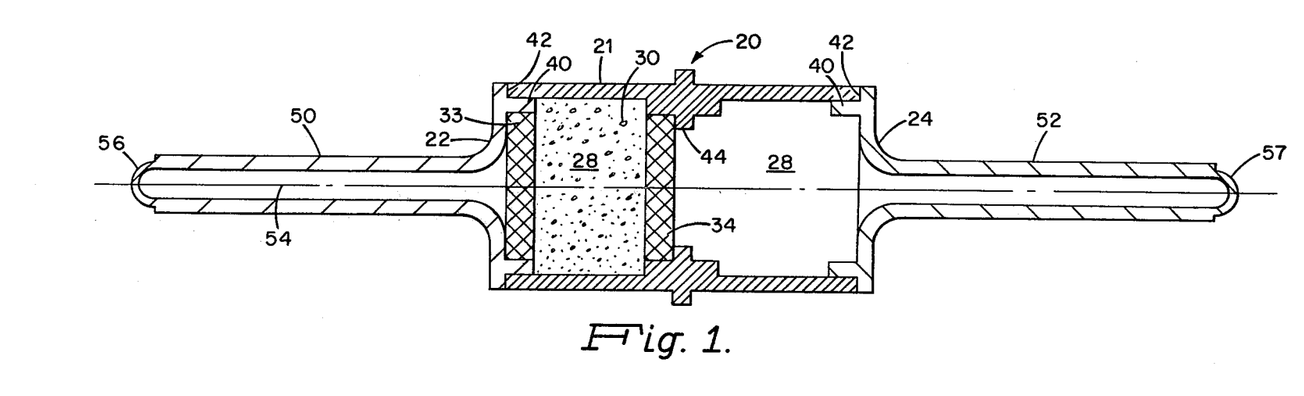
FIG. 1 is a sectional view of a molecular sieve trap according to a preferred embodiment of the invention.

FIG. 1 shows a cross-sectional view of a molecular sieve trap 20 according to the invention. The trap is uniquely suited for passing NO and $NO_2$ gases in a gas stream directed through the trap while selectively trapping substances including double-bonded carbon compounds such as ethylene, sulfur compounds such as hydrogen sulfide, and vinyl halides such as vinyl chloride. Removal of these substances from a gas stream facilitates accurate measurement of its NO and $NO_2$ contents.

The trap preferably comprises a cartridge 20 including a generally cylindrical, open-ended shell 21, an inlet end cap 22 and an outlet end cap 24. The shell 21 and the caps 22 and 24 are fabricated from nylon or other suitable material and when connected together define a cavity 28 for holding one or more packings. In one preferred arrangement as shown in FIG. 1 the upstream portion of the cavity contains a packing 30 while the downstream portion of the cavity adjacent to the outlet end cap 24 is left unfilled. To prevent escape of the packing 30 from the cavity 28 during handling or use of the trap 20, a porous retainer or plug 33 is provided between the inlet end cap 22 and the packing 30, and a similar plug 34 is provided at the downstream end of the packing 30.

The packing 30 within the cavity 28 comprises a dry granular adsorbent material with a unique sieve-like selectivity such that it passes NO and $NO_2$ gases contained in a gas stream directed through the trap 20 while trapping and retaining certain other substances with larger and/or more polar molecules. A preferred material for the packing 30 is Type 13X Union Carbide Molecular Sieve adsorbent, available from Union Carbide Corporation's National Specialty Gas Office, South Plainfield, N.J. The Type 13X material is a synthetic, crystalline, activated sodium alumino-silicate having the unit cell formula $$Na_{86}[(AlO_2)_{86}(SiO_2)_{106}]\cdot 276H_2O$$

and having uniformly sized pores of nominal diameter equal to ten angstroms. This material, or another zeolite or molecular sieve adsorbent having pores of about ten angstrom size, will exclude from passage therethrough molecules having an effective diameter greater than ten angstroms. In addition, it will trap certain other substances based on a preference for retaining polar or polarizable molecules.

The Type 13X material for the packing 30 may be obtained in the form of powder, beads, or pellets which then are mechanically ground and/or sieved as needed to obtain particles of a size suitable for use in the trap 20. A currently preferred packing 30 for the trap is Type 13X molecular sieve material of 60 to 80 mesh size. Particles as small as about 600 mesh size have performed satisfactorily as a packing 30, but are less preferred than the 60 to 80 mesh size particles. Large particles, such as those with dimensions of one-sixteenth inch or larger do not provide acceptable trapping selectivity, and in fact have been found in tests to trap or retard passage of NO gas.

In one trap found suitable for use as described in the present invention, the portion of the cavity 28 filled by the packing 30 comprises a cylinder having a diameter of about three-fourths of an inch and a length (between the plugs 33 and 34) of about one-half inch.

The cavity 28 of the molecular sieve trap 20 may contain a single packing 30 as shown in FIG. 1, in which case the unfilled portion of the cavity between the packing 30 and the outlet end cap 24 serves as a vacuum chamber reservoir during use of the trap in a system for detecting nitrogen compounds such as N-nitrosamines. This reservoir or unfilled cavity has proven effective in helping to maintain constant vacuum levels in systems such as that shown in FIG. 4 wherein vacuum is applied by a pump located downstream of the trap 20. This has assisted in eliminating drift in the baseline level of output signals of the system and in improving its detection sensitivity.

In an alternate trap configuration (FIG. 2) the packing 30 is positioned in the downstream portion of the cavity 28 of a trap 31, and a second packing 32 is provided between the packing 30 and the inlet end cap 22. The packing 32 comprises a sorbent material for removing water vapor from a gas stream prior to the passage of the gas stream into the packing 30. Removal of the water prevents it from being trapped in and clogging the pores of the molecular sieve material, which would impair the effectiveness of the packing 30 as a selective trap. The sorbent material of the packing 32 may be any material which is capable of removing moisture from the gas stream without trapping NO gas or reacting with substances in the gas stream. Suitable materials are granular sodium sulfate, calcium sulfate, phosphorous pentachloride, aluminum silicates, or combinations thereof.

Figure 2:
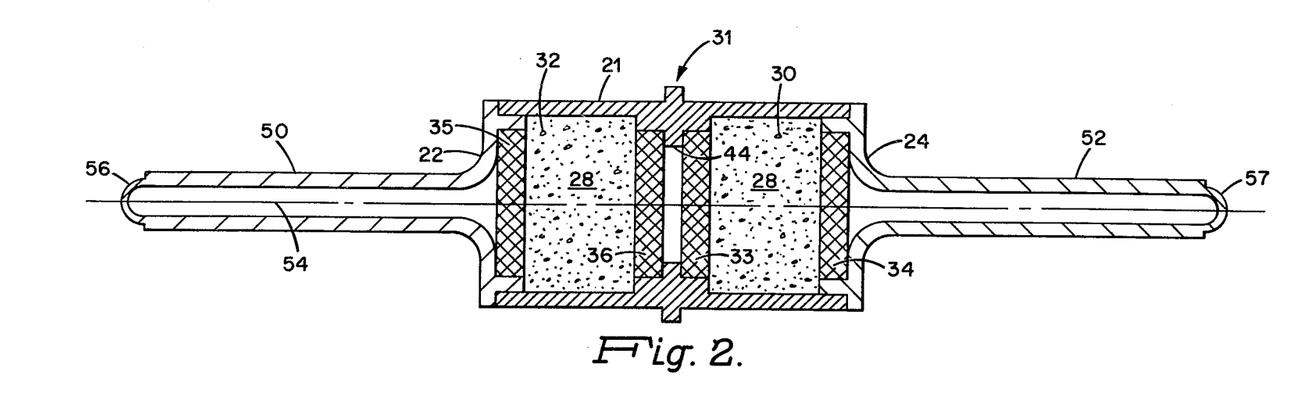
FIG. 2 is a sectional view of a molecular sieve trap according to another embodiment of the invention.

To assure retention of the packing 32 within the cavity 28 of the trap 31, porous retainers or plugs 35 and 36 similar to the plugs 33 and 34 are provided adjacent to the ends of the packing 32. One suitable material for the plugs 33, 34, 35 and 36 is polyethylene in the form of beads of 240 mesh size pressed to form a layer about one-eighth of an inch thick. Plastic plugs are preferable to metal screens as retainers because plastic plugs have only a minor effect on the packings 30 and 32 during ultrasonic welding of the end caps 22 and 24 to the shell 21 to form the trap. Metal screens by contrast, may vibrate during ultrasonic welding and abrade some of the packing materials into dust, thus decreasing effectiveness of the trap.

Each of the end caps 22 and 24 includes a collar 40 at one end which fits tightly within the open ends of the shell 21. To form a sealed, vacuum-tight trap, the end caps are joined to the shell by, for example, ultrasonically welding the annular end face 42 of each cap to one end of the shell 21. The welding locations and the tight frictional fit between the collar 40 of each end cap and the inner wall of the shell 21 isolates the packings 30 and 32 from the welding sites, thus reducing the risk of contaminating these packings during joining of the caps 22 and 24 to the shell 21. The possibility of contamination is further minimized by appropriate selection of materials for the caps 22 and 24 and the shell 21. In general, these components may be made of any rigid material such as plastic or metal, but nylon is preferred since it is readily moldable and does not outgas during either ultrasonic welding of the end caps and the shell or during subsequent use of the trap 20 or 31 to selectively remove substances from a gas stream.

Although two identical caps 22 and 24 are indicated in the traps 20 and 31 it may be desirable, particularly when the trap includes two different packings, to alter the shape of one cap, or clearly label it, to help assure proper orientation of the trap with respect to an incoming gas stream during use—i.e., so that the gas stream is directed through the moisture-removing packing 32 prior to contacting the packing 30. Also, one of the end caps 22 and 24 may be formed integrally with the shell 21 to reduce the number of parts and welding operations required to form the trap. If an integral shell-and-cap design is to be used with a trap configuration having two packings, it may be desirable to eliminate the annular support 44 which projects from the inner wall of the shell 21 in order to permit convenient loading of the packings and the required plugs into the cavity 28 prior to welding of the shell 21 and the reamining cap.

To facilitate connection of the trap to a tube or line carrying a gas stream whose NO or $NO_2$ content is to be determined, the end caps 22 and 24 include tubelike, elongated portions 50 and 52, respectively, which extend outwardly from the shell 21 of the assembled trap 20 along a central axis 54 thereof. The elongated portions terminate with closed ends 56 and 57 which prevent moisture and other contaminants from contacting thg packings 30 and 32 during storage or shipment of the trap. When it is desired to use the trap for selective filtering of a gas stream, the closed ends of the trap are removed as by severing. Then the resulting open-ended elongated portions are attached by vacuum-tight fittings to a line carrying a gas stream to be received through the inlet end cap 22 of the trap and to another line for carrying the gaseous effluent of the trap away through the outlet end cap 24 of the trap.

Figure 3:
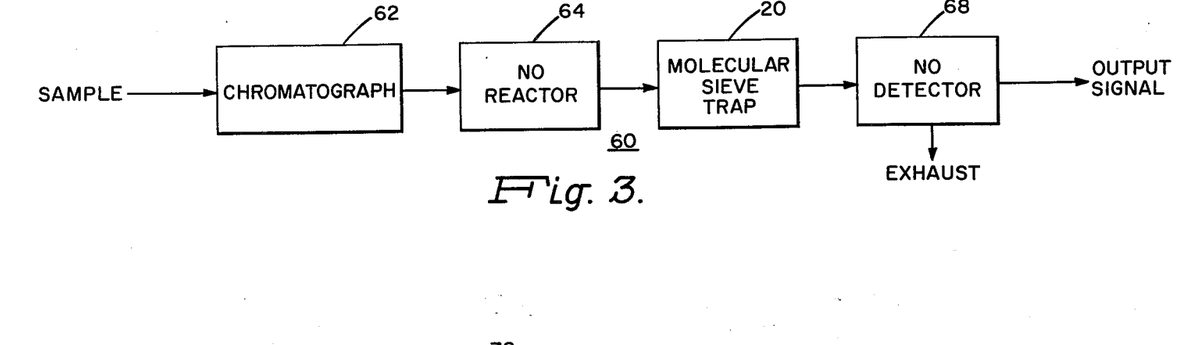
FIG. 3 is a block diagram of a system for detecting nitrogen compounds according to a preferred embodiment of the invention.

FIG. 3 shows a block diagram of a nitrogen compound detection system 60 incorporating the currently preferred molecular sieve trap 20 as an essential component. The system 60 comprises, in series arrangement, a chromatograph 62, an NO reactor 64, a molecular sieve trap 20, and a NO detector 68. A sample to be tested for certain nitrogen compounds such as N-nitroso compounds is directed in liquid or gaseous form to the chromatograph 62, which serves to separate the sample into different portions and to produce an effluent including, at different intervals of time, a first portion containing the nitrogen compounds to be detected and a second portion without these nitrogen compounds. The NO reactor 64 receives the effluent of the chromatograph 62 and applies energy to the first portion thereof in an amount sufficient to selectively release NO gas from the nitrogen compounds to be detected. The NO reactor 64 may, for example, be a non-catalytic pyrolyzer or may comprise a temperature-controlled reaction chamber with a source of ultraviolet radiation therein. The gaseous products of the NO reactor 64 are applied to the molecular sieve trap 20, which passes substantially all of the NO gas in these reactor products to the NO detector 68 while retaining substances which might interfere with proper operation of the NO detector 68. The effluent of the trap 20 is then applied to the detector 68 which may be a chemiluminescent detector, a mass spectrometer tuned to the mass of NO, an instrument for measuring radiation absorption of NO gas, or any other suitable NO detector. The NO detector 68 accurately measures the NO content of the trap effluent, and in particular measures the concentration of NO gas released from the first sample portion, and furnishes a direct indication of the amount and identity of the nitrogen compounds to be detected.

Figure 4:
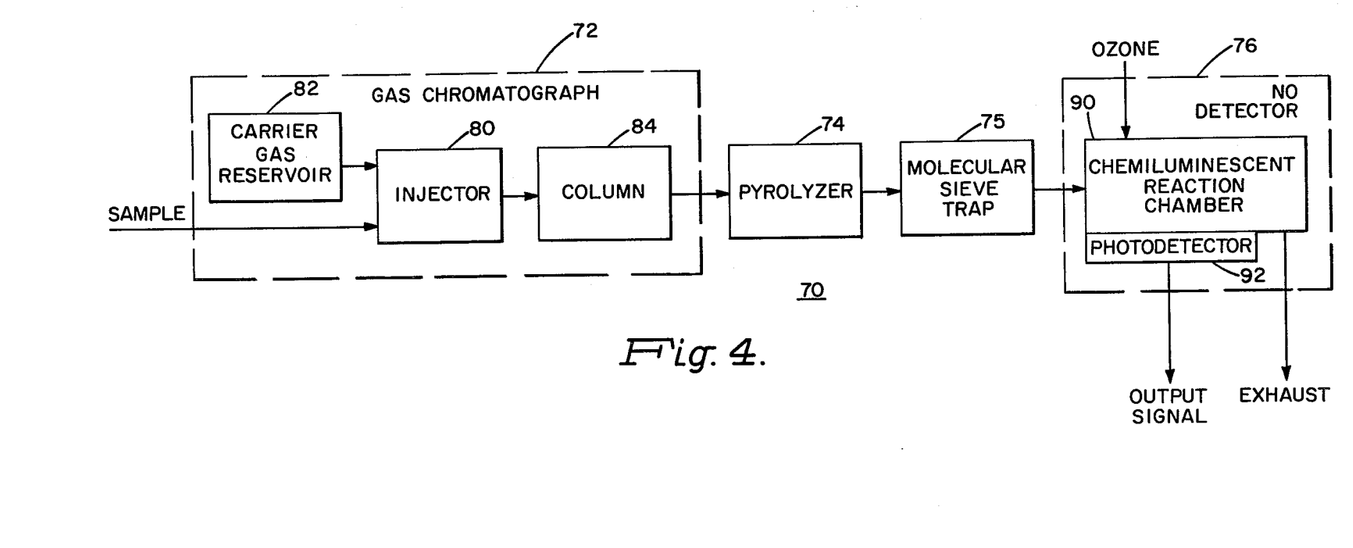
FIG. 4 is a block diagram of a system for detecting N-nitrosamines and certain other nitrogen compounds of a sample according to a preferred embodiment of the invention.

A preferred system for detecting nitrogen compounds, particularly N-nitroso compounds, contained in a sample is shown in block diagram form in FIG. 4. The system 70 comprises a gas chromatograph 72 arranged in series with a pyrolyzer 74, a molecular sieve trap 75, and a NO detector 76.

The gas chromatograph 72, which may be one of many known types which provide a sample flow rate on the order of 4–200 cc/minute, receives a sample in either gaseous or liquid form and produces a timewise separation in the flow of certain portions of the sample through the remaining components of the system. The sample is first supplied to an injector 80 of the chromatograph 72 which also receives a carrier gas such as helium or argon from a carrier gas reservoir 82. Then the carrier gas and sample are injected into a column 84 (if the sample is received as a liquid by the chromatograph 72, it is vaporized near the inlet of the column 84). The column 84 operates to separate the gaseous sample so that the effluent of the chromatograph 72, includes, at different intervals of time, a first portion containing N-nitroso compounds (hereinafter termed the N-nitroso portion) and a second portion without N-nitroso compounds (hereinafter termed the non-N-nitroso portion). Such separation is necessary since otherwise certain nitrates, nitrites, or other compounds in the sample might break down to produce NO gas in the pyrolyzer 74 at the same time as NO is intentionally liberated therein from N-nitroso compounds, which would hinder accurate detection of the NO liberated by the N-nitroso compounds. The column 84 also produces a timewise separation between different N-nitroso compounds in the N-nitroso portion.

The pyrolyzer 74, which is positioned to receive the effluent of the chromatograph 72, comprises means for selectively liberating NO gas from the N-nitroso portion of the sample by applying an amount of thermal energy sufficient to break the N-NO bonds of the N-nitroso compounds without breaking other molecular bonds in any substantial numbers. A preferred non-catalytic pyrolyzer, described in more detail in the above-referenced U.S. Pat. No. 3,996,002, includes a cylindrical tube with ceramic, chemically inert interior walls. The pyrolyzer 74 also includes, or has associated therewith, a temperature controller such as an electric heater which surrounds the tube and is capable of maintaining a desired temperature such as about 300° C. to 500° C. within the tube.

The gaseous effluent of the pyrolyzer 74 is applied to a molecular sieve trap 75 such as the trap 20 containing a packing 30 (FIG. 1). Substantially all of the NO gases in the pyrolyzer effluent, including, most importantly, the NO gas liberated from the N-nitroso portion of the sample, pass through the trap 75 and into the NO detector 76. $NO_2$ gas also passes through the trap 75 but does not interfere with detection of NO gas. However, certain compounds having molecules which are larger and/or more polar than NO are retained by the trap 75 so that they cannot interfere with subsequent measurement of NO gas in the detector 76.

In the preferred N-nitroso compound detection system 70 illustrated in FIG. 4, the detector 76 for measuring the amount of NO gas which is produced by pyrolysis of the sample comprises a chemiluminescent ozone reaction detector such as a Model 10-A NO—$NO_x$ analyzer manufactured by Thermo Electron Corporation, Waltham, Massachusetts. The detector 76, which typically is arranged to operate at a pressure in the range of 0.5 –20 mm. Hg, includes a chemiluminescent reaction chamber 90 for receiving and combining a stream of ozone and the effluent of the molecular sieve trap 75. A chemiluminescent reaction occurs in the chamber 90 between the ozone and any NO gas present. The intensity of this reaction, as sensed and converted to an electrical output signal by a photodetector 92, is directly indicative of the quantity of NO gas input to the detector 76 and thus of the N-nitroso compounds present in the sample.

Figure 5:
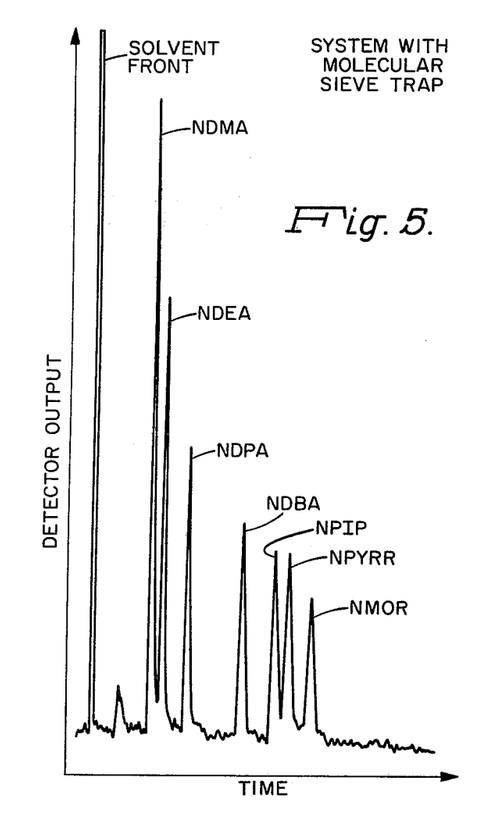
FIGS. 5 and 6 are chromatograms obtained in tests conducted on samples containing several known N-nitroso compounds and which illustrate results obtained using a detection system with a molecular sieve trap according to the present invention (FIG. 5) and a prior art N-nitroso compound detection system including a cold trap (FIG. 6).
Figure 6:
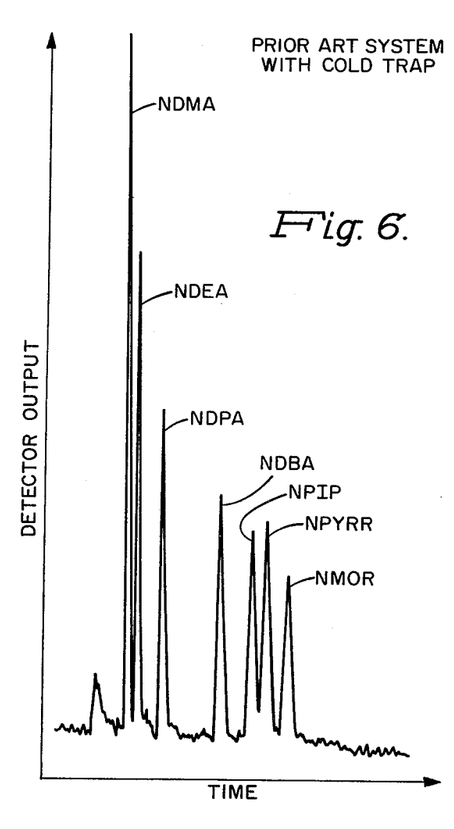

Reference is made to FIGS. 5 and 6 which are chromatograms or plots versus time of the output of the NO detector 76 obtained in tests conducted to determine the effectiveness of the system of the present invention in measuring the N-nitroso compound content of a sample. Local peaks in these output signals indicate the presence of N-nitroso compounds tested, and the areas under each peak are indicative of the relative concentrations of these compounds. FIG. 5 shows test results obtained when five microliters of a solution of acetone containing 0.625 nanograms each of seven N-nitroso compounds was input to the detection system 70 including a molecular sieve trap with a single packing of 60 to 80 mesh Type 13X molecular sieve material. The N-nitroso compound tested were the following: N-nitroso-dimethylamine (NDMA), -diethylamine (NDEA), -dipropylamine (NDPA), -dibutylamine (NDBA) -piperdine (NPIP), -pyrrolidine (NPYRR), and -morpholine (NMOR). FIG. 6 shows results obtained when a similar sample was input to a detection system with a cold trap substituted for the molecular sieve trap 75.

The nearly identical plots of detector output versus time, both clearly showing detection of the seven N-nitroso standards, demonstrate that the molecular sieve trap 75 passes the NO gas input thereto from the pyrolyzer 74 to permit accurate detection of N-nitroso compounds.

Figure 7:
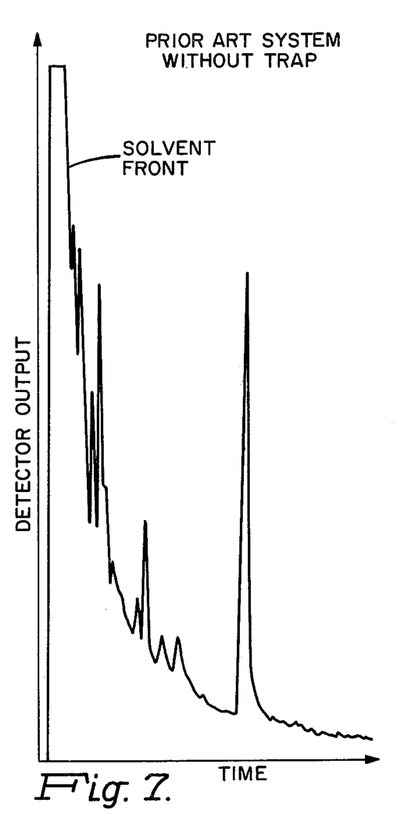
FIGS. 7-9 are chromatograms obtained in tests conducted on samples collected from an industrial plant and which illustrate results obtained using: a prior art detection system with no trap (FIG. 7), a prior art detection system with a cold trap (FIG. 8), and a detection system with a molecular sieve trap according to the present invention (FIG. 9).
Figure 8:
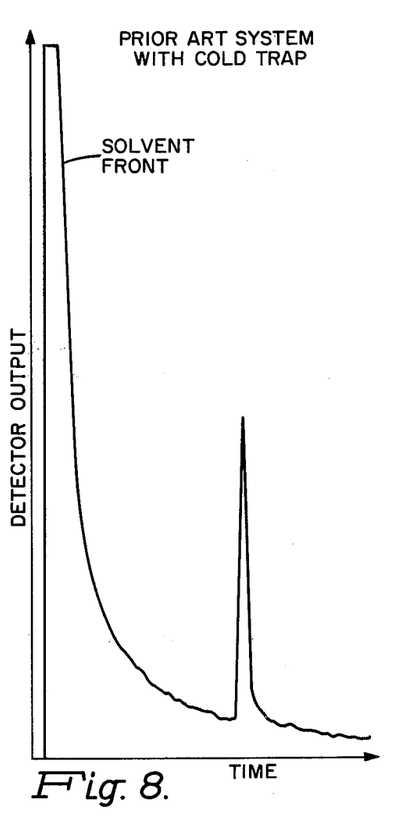
Figure 9:
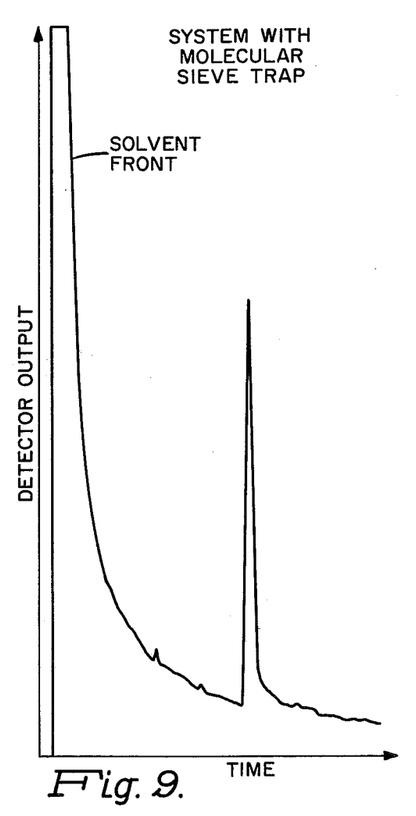

FIGS. 7–9 show plots versus time of the output of a NO detector obtained from tests of equal portions of a liquid sample input to two prior art nitrogen compound detection systems and to the system 70 of the invention.

The liquid sample was obtained by passing a solvent through an air-sampling cartridge which had previously monitored air in an industrial plant. FIG. 7 illustrates test results from a prior art system differing from the system 70 in that it did not include a trap between the pyrolyzer 74 and the NO detector 76; FIG. 8 shows results from a prior art system including a cold trap; and FIG. 9 shows test results from the system 70 including a molecular sieve trap 75 with a single packing of 60 to 80 mesh Type 13X molecular sieve material.

When no trap was used, the output of the NO detector 76 (FIG. 7) showed numerous peaks. By contrast, when either a cold trap or the molecular sieve trap of the present invention was included in the nitrogen compound detection system, the output (FIGS. 8 and 9) of the NO detector contained only a single peak. This single peak revealed the presence of an N-nitrosamine and also indicated that the sample in fact included but a single NO-producing compound. These plots shows that the molecular sieve trap is effective (and so also is the cold trap in this instance) in removing non-NO producing compounds from the pyrolyzer effluent of a nitrogen compound detection system.

The data set forth above, and results of other tests, confirm the utility of the molecular sieve trap for selectively trapping substances in a gas stream, particularly in a system for detecting certain nitrogen compounds such as N-nitroso compounds in a sample. This trap, when packed with a suitable molecular sieve material, readily passes NO and $NO_2$ gas while retaining larger and/or more polar molecules. The materials trapped include substantially all known compounds whose presence in a NO detector could interfere with accurate detection of NO gas such as by producing a chemiluminescent reaction similar to that of NO gas. In addition, the molecular sieve trap removes dust and dirt particles which may be present in a gas stream such as the effluent of a pyrolyzer of a N-nitroso compound detection system. This assists in keeping clean any light-transmitting elements of the NO detector contacting the trap effluent such as the lens of a photodetector in a chemiluminescent detector and helps to eliminate noise in the electrical output of the detector. In tests conducted to compare operation of the N-nitroso compound detection system 70 of the present invention with a prior art system differing only in its inclusion of a cold trap instead of a molecular sieve trap, the molecular sieve trap has been found to provide NO detector output signals with higher signal-to-noise ratios. Thus a system with the molecular sieve trap provides increased sensitivity, which permits accurate detection of very low concentrations (a few parts per billion ) of N-nitroso compounds. Also, for detection of low levels of nitrogen compounds, the molecular sieve trap simplifies sample preparation—for example, its use in a N-nitroso compound detection system eliminates the need to pre-concentrate certain samples, as by solvent extraction, prior to their analysis.

In contrast to the cold traps used in systems for detecting N-nitroso compounds, the molecular sieve trap requires virtually no maintenance. Moreover, unlike cold traps, when the effectiveness of the molecular sieve trap to selectively retain materials diminishes, this is clearly indicated by a distinct spreading or broadening of the peaks in the detector output signal. At the onset of evidence of band-spreading or at predetermined intervals such as at the beginning of each 24-hour period of use, the molecular sieve trap may be quickly and easily uncoupled from the tube or other sample passage line extending between the pyrolyzer and the NO detector of a nitrogen compound detection system such as the system 70 of the invention, and a fresh sieve trap may be substituted for the spent trap.

Another important use of the molecular sieve trap in detection of nitrogen compounds is in combination with, or as part of, a detector for measuring the concentration of oxides of nitrogen such as NO and $NO_2$ present in a gaseous sample. The trap, when positioned in a sample inlet line of a $NO_x$ detector ($NO_x$ being defined herein as the total amount of NO and $NO_2$ gases in a sample), acts as a filter to readily pass NO and $NO_2$ while removing compounds which could interfere with accurate measurements of the $NO_x$ content of the sample.

Figure 10:
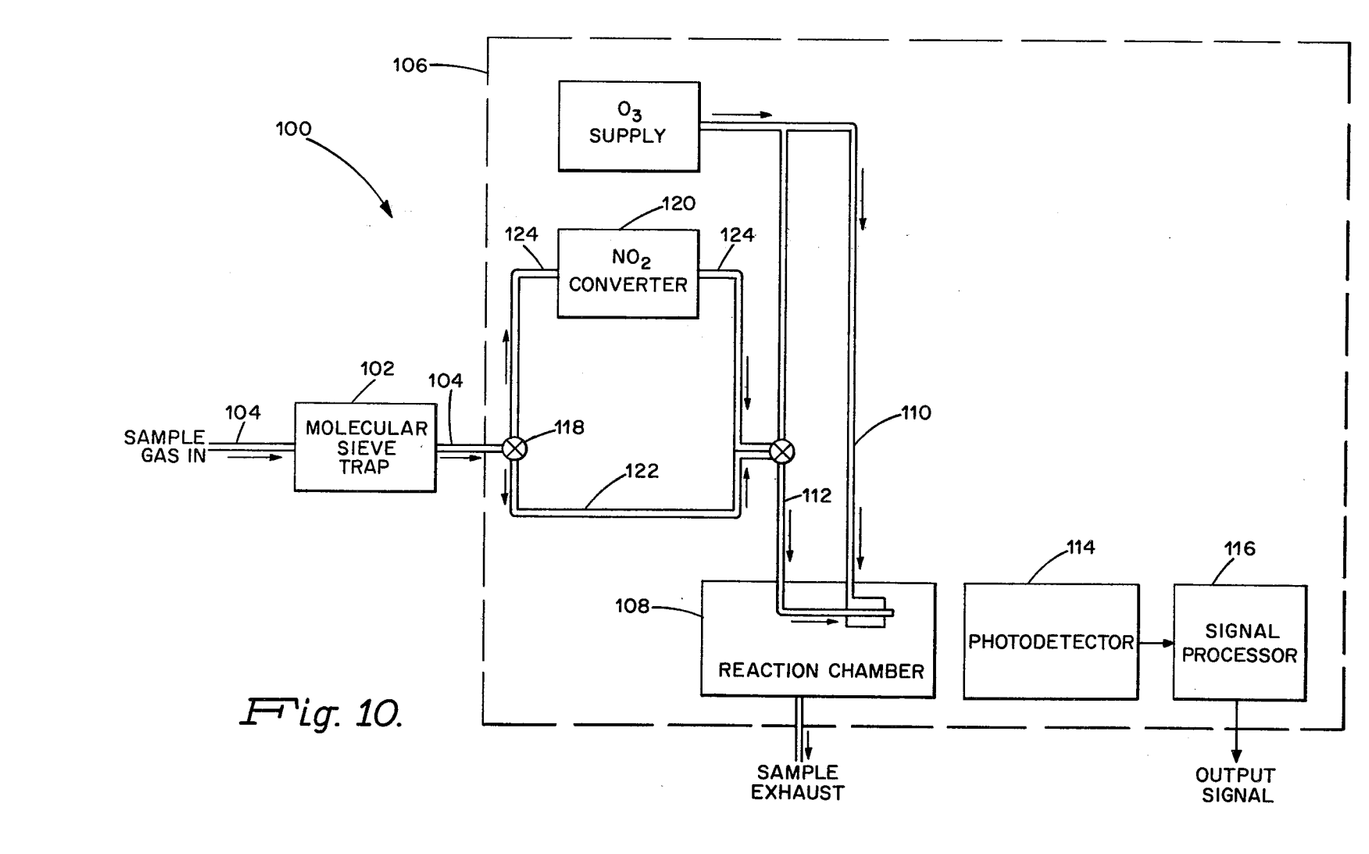
FIG. 10 is a block diagram of a $NO_x$ detection system according to a preferred embodiment of the invention.

FIG. 10 shows a simplified block diagram of a preferred $NO_x$ detection system 100 incorporating a molecular sieve trap 102 in a sample inlet line 104 of a chemiluminescent analyzer 106. The trap 102 may contain a single packing of a sodium alumino-silicate molecular sieve material such as Type 13x material, whose particles have pores of nominal diameter equal to about 10 angstroms. Alternatively, the trap may contain two packings, the additional packing being asorbent material for removing water vapor from the gas stream as described earlier in connection with FIG. 2 hereof. When a gas sample containing NO and/or $NO_2$ is directed into the trap 102, NO and $NO_2$ pass through the trap and to the analyzer 106 while compounds of large molecular size or high polarity relative to NO and $NO_2$—e.g. compounds such as vinyl chloride, hydrogen sulfide, ethylene and other unsaturated hydrocarbons, and nitrosamines—are retained in the trap 102. Thus these latter compounds are unavailable to mimic NO or $NO_2$ in a subsequent chemiluminescent reaction.

The chemiluminescent analyzer 106 includes a reaction chamber 108 to which ozone and a gas sample are furnished, e.g. through concentric portions of tubes 110 and 112 respectively. A photodetector 114 is provided for monitoring the chemiluminescent reaction between the ozone and the NO gas of the sample, and a signal processor 116 is connected to the photodetector 114 for processing its signals to compute the $NO_x$ content of the sample.

To permit determination of both the NO and $NO_2$ contents of a gas sample, the chemiluminescent analyzer 106 includes a valve 118 and an $NO_2$ converter 120 (which may be any of several commercially available reactive or catalytic devices for converting $NO_2$ gas to NO gas). For calculation of NO gas content, the valve 118 is positioned to channel the gaseous effluent of the trap 102 through the conduit 122 directly to the reaction chamber 108. Since the $NO_2$ gas in the sample does not readily react with ozone in the chamber 108, the output signal of the photodetector 114 for this mode of operation is indicative of the NO content of the sample.

Alternatively, the valve 118 may be positioned so that the sample is directed through a conduit 124 and through the $NO_2$ converter 120 prior to its entry into the chamber 108. In this mode, any $NO_2$ in the sample is converted to NO and the output signal of the photodetector 114 is indicative of the total $NO_x$ content of the sample. The signal processor 116 may compute the $NO_2$ content of the sample by subtracting the NO content from the $NO_x$ content.

Figure 11:
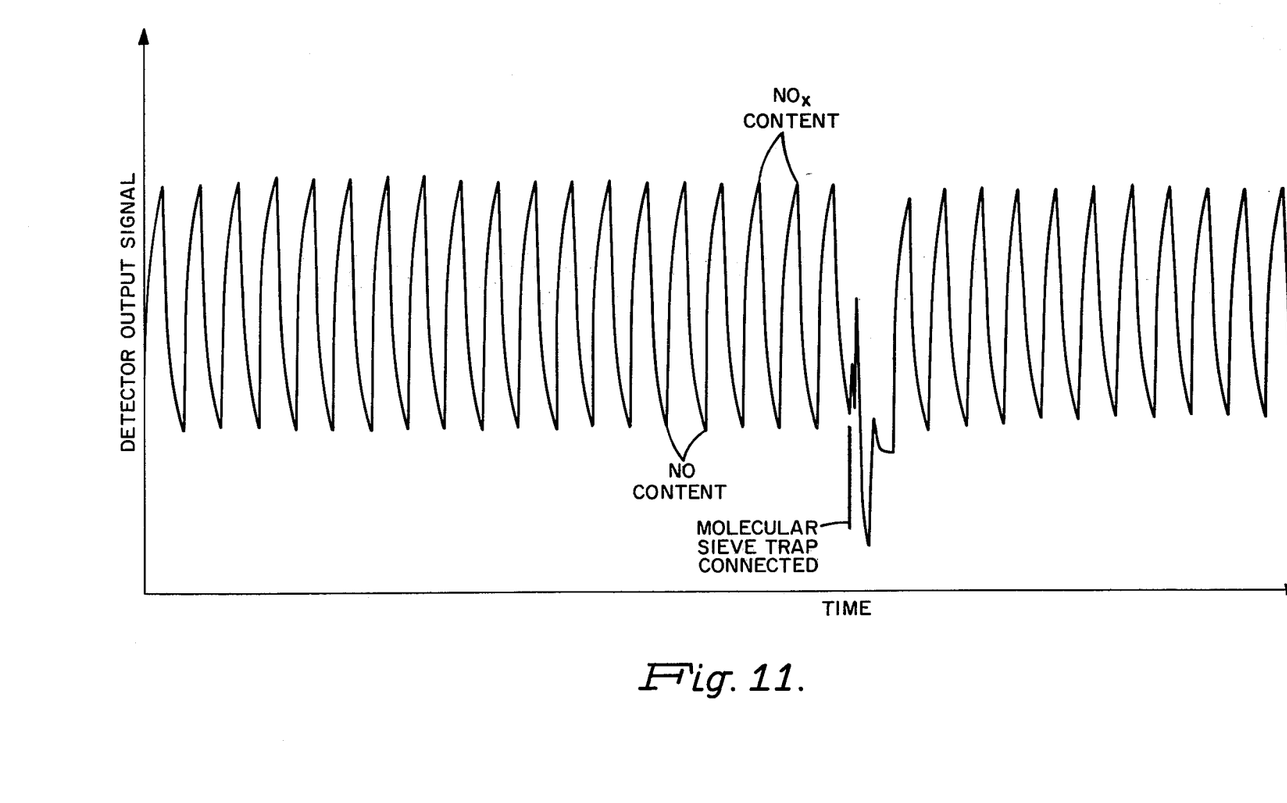
FIG. 11 is a plot of output signal versus time from a test of a known sample in a $NO_x$ detection system of the invention.
Figure 12:
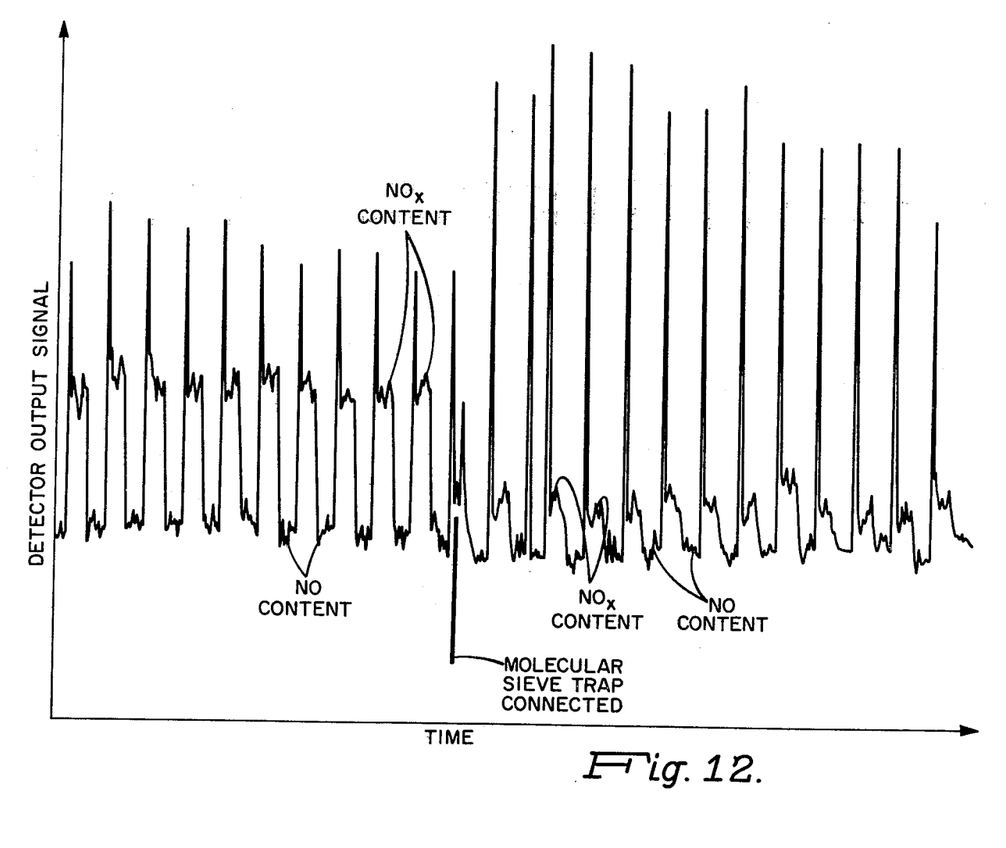
FIG. 12 is a plot of output signal versus time from a test of a gas sample from an automobile exhaust in a $NO_x$ detection system of the invention.

FIGS. 11 and 12 are output signals of the $NO_x$ and NO concentrations measured in tests conducted on gas samples using a $NO_x$ detector system similar to the system 100 shown in FIG. 10. The test system, however, also included means for either connecting the molecular sieve trap 102 to the inlet line 104 to filter the inlet flow of a gas sample or disconnecting it therefrom to pass the sample unfiltered to the analyzer 106. The molecular sieve trap employed in these tests comprised a cylindrical cartridge containing a single packing of 60 to 80 mesh Type 13x molecular sieve material. For each test the system was first operated without the trap, then at the times indicated in FIGS. 11 and 12, the trap was connected to thereafter selectively filter the gas sample being analyzed. During both tests, the valve 118 was switched at regular intervals to first direct flow through the conduit 122 and then to direct flow through the conduit 124 and the $NO_2$ converter 120. As a result, the output signals of FIGS. 11 and 12 exhibit an alternating succession of peaks whose levels are indicative of the $NO_x$ content of the gas sample and valleys whose levels are indicative of the NO content of the sample. FIG. 11 illustrates test results obtained when a sample containing small amounts of NO and $NO_2$ was analyzed. The similarity of the detector output readings before and after the molecular sieve trap was connected to filter the sample indicates that the trap passes NO and $NO_2$ gases and thus does not alter the $NO_x$, NO, or $NO_2$ content of the sample.

The detector output signals of FIG. 12 are results of tests on a gas sample obtained from an automobile exhaust. In this signal trace the spikes or sharp peaks obtained immediately after each switch from measurement of NO to measurement of $NO_x$ are spurious peaks and should be disregarded in reading the $NO_x$ content of the sample. One important trend illustrated in the signal trace is the large drop in the $NO_x$ content signal after activation of the molecular sieve trap. This indicates that the trap removed certain substances in the gas stream which, when unfiltered, had erroneously contributed to the measurement of $NO_x$ by the analyzer. For the sample tested, the difference in indicated $NO_x$ content is about twenty percent, which demonstrates the significant improvement in accuracy of $NO_x$ measurements obtainable when the molecular sieve trap is employed. Also, for this particular sample, the improvement is attributable primarily to more accurate measurement of $NO_2$ content since the base level of NO (minimum values of the signal trace of FIG. 12) changed only slightly upon activation of the trap as a sample filter.

While the invention has been shown and described with respect to preferred embodiments thereof, it is apparent that the molecular sieve trap and the nitrogen compound detection system may be embodied in other specific forms without departing from the spirit or essential characteristics of the invention. The scope of the invention is indicated by the appended claims, and all changes which come within the range of equivalency of these claims are intended to be embraced therein.

What is claimed is:

1. Apparatus for selectively trapping substances in a gas stream comprising a cartridge having an inlet at one end for receiving a gas stream, an outlet at the end opposite said inlet end, and a shell defining a chamber between said inlet and said outlet, said chamber containing a packing of a granular molecular sieve material permeable to the flow therethrough of NO gas and adapted to trap and hold substances therein which might otherwise interfere with measurement of the NO gas which has passed through said packing.

2. Apparatus as in claim 1 wherein said molecular sieve material has a nominal pore diameter of about 10 angstroms.

3. Apparatus as in claim 1 or 2 wherein said molecular sieve material is a crystalline sodium alumino-silicate material.

4. Apparatus as in claim 1 wherein said chamber contains, in addition to said packing of granular molecular sieve material, a second packing of a drying agent between said inlet and said packing of granular molecular sieve material, said drying agent being permeable to the flow therethrough of NO gas and adapted to remove water from the gas stream.

5. Apparatus as in claim 4 wherein said drying agent is a granular material selected from the group consisting of sodium sulfate, calcium sulfate, phosphorous pentachloride, aluminum silicates, and combinations thereof.

6. Apparatus as in claim 1 further including porous retainer means adjacent to the inlet and outlet of said cartridge for holding said packing in said chamber.

7. Apparatus as in claim 1 and 2 wherein said particles are of 60 to 80 mesh size.

8. Apparatus for measuring in a sample the amount of predetermined nitrogen compounds comprising:
a chromatograph for receiving said sample and producing an effluent including, at separate intervals of time, a first portion containing said predetermined nitrogen compounds and a second portion without said compounds;
a reactor for selectively liberating NO gas from the nitrogen compounds of said first portion, thereby producing a reactor effluent containing NO gas;
a NO detector for measuring the amount of NO gas liberated in said reactor; and
a trap between said reactor and said detector for selectively trapping substances from said reactor effluent, said trap including a packing of a granular molecular sieve material permeable to the flow therethrough of NO gas and effective to trap and hold substances whose presence in said detector might interfere with measurement of the NO gas liberated by said reactor.

9. Apparatus as in claim 8 wherein said predetermined nitrogen compounds are N-nitroso compounds having the general formula wherein $R_1$ and $R_2$ are the same or different organic radicals, including those radicals which together with the non-nitroso N of the depicted N—NO bond constitute a nitrogen heterocyclic radical; and wherein said reactor is operable to selectively liberate NO gas from said N-nitroso compounds by breaking the N—NO bonds of said N-nitroso compounds.

10. Apparatus as in claim 9 wherein said reactor comprises a pyrolyzer for heating the N-nitroso compounds with an amount of thermal energy effective to break the N—NO bonds thereof.

11. Apparatus as in claim 8 wherein said molecular sieve material comprises particles having pores with a nominal diameter of about 10 angstroms.

12. Apparatus as in claim 11 wherein said molecular sieve material is a crystalline sodium alumino-silicate material.

13. Apparatus as in claim 8 wherein said particles are of 60 to 80 mesh size.

14. Apparatus as in claim 8 wherein said chromatograph comprises a gas chromatograph including a column and means for driving a mixture of said sample and a carrier gas through said column.

15. Apparatus as in claim 8 wherein said trap comprises a cartridge having an inlet for receiving said reactor effluent, an outlet, and a cylindrical shell defining a chamber between said inlet and said outlet, said chamber containing said packing of molecular sieve material and also containing, between said inlet and said packing of molecular sieve material, a second packing of a drying agent permeable to the flow therethrough of NO gas and adapted to remove water from said reactor effluent.

16. Apparatus for measuring in a gaseous sample the concentration of at least one oxide of nitrogen comprising:
a reaction chamber for permitting a chemiluminescent reaction therein of a selected constituent of the sample with a reagent;
means for supplying said reagent and said gaseous sample to the reaction chamber;
means for detecting the light produced in said chamber during a chemiluminescent reaction; and a trap for selectively removing substances from said gaseous sample prior to entry of said sample into said reaction chamber, said trap comprising a packing of a granular molecular sieve material permeable to the flow therethrough of NO and $NO_2$ gases and effective to trap and hold substances whose presence in said reaction chamber might interefere with measurement of NO or $NO_2$ gas in said sample.

17. Apparatus as in claim 16 wherein said molecular sieve material comprises particles having pores with a nominal diameter of about 10 angstroms.

18. Apparatus as in claim 16 wherein said reagent is ozone and said selected constituent of the sample is NO gas.

19. Apparatus as in claim 16 wherein said molecular sieve material comprises particles of a crystalline sodium alumino-silicate material of 60 to 80 mesh size.

20. Apparatus as in claim 19 wherein said trap further comprises a packing of a drying agent permeable to the flow therethrough of NO and $NO_2$ gases and operable to remove water from said sample prior to passage of said sample through said packing of molecular sieve material.

21. Apparatus as in claim 16 further including an $NO_2$ converter between, and in fluid communication with, said trap and said reaction chamber for converting $NO_2$ gas in said sample to NO gas, thereby to permit measurement of the total concentration of NO gas and $NO_2$ gas of said gaseous sample.

* * * * *